United States Patent [19]

Heverhagen

[11] Patent Number: 5,271,942
[45] Date of Patent: Dec. 21, 1993

[54] AGENT FOR REDUCING THE GROWTH OF OR REMOVING THE HAIR ON THE HUMAN BODY

[76] Inventor: Ulrich Heverhagen, Postfach 13 48, DE-7760 Radolfzell, Fed. Rep. of Germany

[21] Appl. No.: 674,791

[22] Filed: Mar. 25, 1991

[30] Foreign Application Priority Data

Dec. 5, 1990 [DE] Fed. Rep. of Germany ....... 4038693

[51] Int. Cl.$^5$ .............................................. A61K 9/48
[52] U.S. Cl. .................. 424/451; 424/195.1; 424/70
[58] Field of Search .................... 424/72, 71, 73, 70, 424/451, 195.1

[56] References Cited

U.S. PATENT DOCUMENTS

| 4,842,610 | 6/1989 | Gordon et al. | 106/162 |
| 4,867,967 | 9/1989 | Crutcher | 424/78.07 |
| 4,879,119 | 11/1989 | Konno et al. | 424/448 |
| 4,981,682 | 1/1991 | Boothroyd et al. | 424/72 |

Primary Examiner—Thurman K. Page
Assistant Examiner—Leon R. Horne
Attorney, Agent, or Firm—Bachman & LaPointe

[57] ABSTRACT

An agent for reducing the growth of human hair comprising a basic substance for application to the skin which contains a urea and demineralized, sterilized water.

15 Claims, No Drawings

AGENT FOR REDUCING THE GROWTH OF OR REMOVING THE HAIR ON THE HUMAN BODY

The invention relates to an agent for reducing human hair growth.

Hairs are threadlike structures on the outer skin of animals and humans and are essentially composed of a horny substance. In the case of human hair, an onion-shaped hair root is located in the hair follicle on a small bulb, the hair papilla, which is rich in blood vessels. The hair receives nutrition therefrom and continues to grow as hair shaft. Small sebaceous glands open into the hair follicle.

The hair is composed of horn cells which are arranged in a medullary and cortical layer and are covered by a cuticle.

As a rule, normal hair growth is tolerated. However, excessive hair growth is upsetting in many cases. Attempts are made in such cases to reduce the hair growth or remove hair from entire areas of the body. Various methods are known for this. On the one hand, mention may be made of mechanical methods in which, for example, tweezers are used to pull out individual hairs. This is painful on the one hand, and very time-consuming on the other. Furthermore, this method entails the risk of causing a wound into which bacteria or the like can penetrate.

Furthermore, there is shaving, in which only the hairs are cut off but grow again after a short time, and usually more strongly.

A method with a hot or cold wax is also known, in which once again the removal takes place only occasionally and, in particular, skin irritation occurs too. In the case of cold wax, the hairs are likewise torn out, which in turn is very painful.

In addition, there are on the market creams, powders, depilatory lotions or milks, but none of these is particularly effective and they are, as a rule, very aggressive.

The inventor's object was to develop an agent of the abovementioned type which can be used to remove hairs effectively and entails, in particular, no attack on the skin.

This object is achieved by a basic substance for application to the skin, in particular demineralized and sterilized water, containing a urea.

This agent has, in particular, the advantageous effect of reducing hair growth on healthy hair. That is to say there is no painful or aggressive treatment of the skin so that no wounds or skin irritation occur here either. There is merely a slowing of hair growth, and this reduction can go so far that hair growth entirely ceases.

Urea is the diamide of carbonic acid and can be prepared by synthesis. It has the effect of denaturing cellular proteins in the hair root and of reducing the function of the hair root. The effect of this is then to diminish growth.

Since, on the other hand, urea is an endogenous substance, it neither damages the skin nor results in irritation. This applies to normal skin. If, however, a hypersensitive skin is to be treated, it has proven advisable also to add plant extracts with a caring affect to the abovementioned basic substance. Particularly suitable for this purpose are hamamelis, arnica and mint. These substances have astringent, tonic, soothing and wound-healing effects.

Similar is true when animal proteins are added to the basic substance. These also have local soothing effects.

For the homogenization of the additives in the basic substance, it has proven advisable also to add to the basic substance a hydro- or propylene glycol. Propylene glycol is an oily, hygroscopic liquid which is prepared by hydration of propylene oxide. It is used in many cases as cosmetic ingredient.

Another improvement in the agent is brought about by adding to the basic substance lactic acid or lactates, i.e. salts of lactic acid. It also has an effect on the metabolic processes in the cells of the hair follicle.

Further addition of Aloe vera gel as moisture donor enhances the effect of the agent according to the invention. Further additives such as methylparaben, PCA (2-pyrrolidone-5-carboxylic acid) serve, in particular, to homogenize and preserve the agent. The ingredient bisabolol, whose main constituent is a camomile extract, has antiinflammatory effects.

In a preferred embodiment, the agent has the following composition:

68–85% by vol. demineralized, sterilized water
0.3–1.2% by vol. urea and/or
0.2–1.0% by vol. animal proteins and/or
0.3–1.2% by vol. plant extracts and/or
6–15% by vol. glycol and/or
0.2–0.3% by vol. lactic acid and/or
 –1.0% by vol. Aloe vera gel and/or
 –0.2% by vol. methylparaben and/or
 –0.1% by vol. PCA and/or
 –0.1% by vol. bisabolol.

Moreover, the agent is administered in various forms. On the one hand, it is to be spreadable on the skin as balsam. In this case, it contains demineralized water in the lower region of the contents stated above, while in addition stearates and stearic acid, in particular, should also be added. These bring about an alteration in the agent to make it balsam-like. In this instance, the agent also contains isopropyl myristate to preserve it. Furthermore, cetyl alcohol and/or dimethicone and/or propylparaben and/or triclosan and/or 2-bromo-2-nitropropane-1,3-diol should also be added.

In a particularly preferred embodiment, the agent also contains in addition imidazolidinylurea, specifically in an amount of from 0.2 to 0.5% by volume. This specific urea has proved in practice to be extremely effective for reducing hair growth.

The agent can furthermore also contain hydroxypropylmethylcellulose (gel former), amino acid and polyquaternium as cationic emulsifier. Besides the balsam form, it is also made available in gel form or in ampoules.

An independent patch test according to Jadassohn and Bloch has shown that no irritation with infiltration or edema, or allergic reactions occurred in test subjects treated with the agent. Accordingly, the agent was designated as "very well tolerated by skin".

It was found, on comparison of hair growth on treated and untreated areas of the body, that the lengths of the hairs which subsequently grew on the treated areas were distinctly smaller than those on the untreated areas of the body.

I claim:

1. An agent for reducing the growth of the hair on the human body, which comprises a substance for application to the skin which contains from 0.3 to 1.2% by volume urea and as a major component thereof demineralized, sterilized water.

2. An agent as claimed in claim 1, wherein the substance also contains plant extracts selected from the group consisting of hamamelis, arnica and mint.

3. An agent as claimed in claim 1, wherein the substance also contains propylene glycol.

4. An agent as claimed in claim 1, wherein the substance also contains a material selected from the group consisting of lactic acid and lactates.

5. An agent as claimed in claim 1, wherein the substance also contains an Aloe vera gel.

6. An agent as claimed in claim 1, wherein the substance also contains a material selected from the group consisting of methylparaben and bisabolol.

7. An agent as claimed in claim 1, wherein the substance comprising 68–85% by vol. demineralized, sterilized water additionally contains a material selected from the group consisting of
   6–15% by vol. glycol,
   0.2–0.3% by vol. lactic acid,
   –1.0% by vol. Aloe vera gel,
   –0.2% by vol. methylparaben,
   –0.1% by vol. PCA and
   –0.1% by vol. bisabolol.

8. An agent as claimed in claim 7, wherein the substance forms a balsam by addition of stearates and stearic acid.

9. An agent as claimed in claim 8, wherein the substance also contains a material selected from the group consisting of isopropyl myristate, cetyl alcohol, dimethicone, propylparaben, triclosan and 2-bromo-2-nitropropane-1,3-diol.

10. An agent as claimed in claim 7, wherein the substance also contains a material selected from the group consisting of
    8–9% by vol. stearates,
    1.8–2.2% by vol. stearic acid,
    5.5–6.0% by vol. cetyl alcohol,
    –0.5% by vol. dimethicone,
    –0.1% by vol. propylparaben,
    –0.1% by vol. triclosan and
    –0.05% by vol. 2-bromo-2-nitropropane-1,3-diol.

11. An agent as claimed in claim 7, wherein the substance additionally contains 0.2–0.5% by volume imidazolidinylurea.

12. An agent as claimed in claim 11, wherein the substance also contains about 1.5% by volume carbomer.

13. An agent as claimed in claim 12, wherein the substance forms a gel by addition of glycol.

14. An agent as claimed in claim 11, wherein the substance contains about 0.25% by volume hydroxypropylmethylcellulose.

15. An agent as claimed in claim 1 wherein the urea is synthetic urea.

* * * * *